(12) United States Patent
Yokoyama

(10) Patent No.: US 6,482,966 B2
(45) Date of Patent: Nov. 19, 2002

(54) CROSSLINK-CYCLIZED CYCLOPENTADIENE AND DIHALOBIS TYPE METAL COMPOUND CONTAINING SAME AS LIGAND

(75) Inventor: Keiichi Yokoyama, Wakayama (JP)

(73) Assignee: Honshu Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 09/773,045

(22) Filed: Jan. 31, 2001

(65) Prior Publication Data

US 2001/0012902 A1 Aug. 9, 2001

(30) Foreign Application Priority Data

Feb. 3, 2000 (JP) .................................. 2000-026835

(51) Int. Cl.[7] .................................................. C07F 17/00
(52) U.S. Cl. ............................ 556/53; 585/20; 585/21; 585/23; 585/27
(58) Field of Search ............................. 556/53; 585/20, 585/21, 23, 27

(56) References Cited

U.S. PATENT DOCUMENTS 6,139,484 A * 10/2000 Biagini et al. ................. 585/27

FOREIGN PATENT DOCUMENTS

| EP | 0 283 739 | 9/1988 |
| EP | 0 760 355 | 3/1997 |
| JP | 10-182714 | 7/1998 |
| JP | 10-316694 | 12/1998 |

OTHER PUBLICATIONS

Austin et al., Journal of Organometallic Chemistry, 491, pp. 11–18 (1995).

* cited by examiner

*Primary Examiner*—Paul F. Shaver
(74) *Attorney, Agent, or Firm*—Wenderoth, Lind & Ponack, L.L.P.

(57) ABSTRACT

A process for producing a crosslink-cyclized cyclopentadiene, comprising the steps of reacting a cyclopentenone with an alkali metal hydride to thereby reduce the cyclopentenone (reduction step A) into a cyclopentenol; and reacting the cyclopentenol with a dehydrating agent to thereby dehydrate the cyclopentenol (dehydration step B) into a crosslink-cyclized cyclopentadiene of the general formula (III):

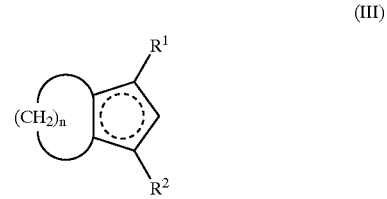

wherein each of $R^1$ and $R^2$ independently represents a hydrogen atom or a linear or branched saturated alkyl group having 1 to 6 carbon atoms, n is an integer of 3 to 10, and the broken line in the 5-membered ring denotes that the 5-membered ring has two double bonds.

8 Claims, 3 Drawing Sheets

CROSSLINK-CYCLIZED CYCLOPENTADIENE AND DIHALOBIS TYPE METAL COMPOUND CONTAINING SAME AS LIGAND

FIELD OF THE INVENTION

The present invention relates to a process for producing a crosslink-cyclized cyclopentadiene, a crosslink-cyclized cyclopentadiene, a dihalobis(η-crosslink-cyclized cyclopentadienyl)metal compound containing the crosslink-cyclized cyclopentadiene, and a process for producing the same.

BACKGROUND OF THE INVENTION

Cyclopentadienes are widely used not only as monomers for producing various polymers but also in the production of metallocene compounds of transition metals such as titanium, zirconium and hafnium. The metallocene compounds are widely utilized as effective ligand components of olefin polymerization catalysts.

Regarding the conventional production of a crosslink-cyclized cyclopentadiene, for example, with respect to the process for producing 1,3-dimethylcyclopentadiene, Japanese Patent Laid-open Publication No. 62(1987)-72630 describes a process comprising reacting dicyclopentadiene with methanol in the presence of an alkali metal oxide. However, this process has a drawback in that the desired product cannot be efficiently obtained due to, for example, by-products of position isomers.

Further, Japanese Patent Laid-open Publication No. 3(1991)-215437 describes a process comprising performing a vapor-phase cyclization dehydration of 5-methyl-5-hexen-2-one in the presence of a catalyst such as alumina. However, this process has drawbacks in that the raw materials are expensive and that the reaction must be performed in a vapor phase at such high temperatures as over 200° C. to thereby necessitate special apparatus.

Still further, Japanese Patent Laid-open Publication No. 8(1996)-208533 describes a process for producing a cyclopentadiene, comprising performing a cyclization dehydration of an unsaturated carbonyl compound in the presence of a solid acid catalyst in a vapor phase. However, this process also has a drawback in that the reaction comprises a cyclization dehydration in a vapor phase and the reaction temperature is as high as 330 to 430° C. (as indicated in working example portions) to thereby necessitate special apparatus.

With respect to a crosslink-cyclized cyclopentadiene of the general formula:

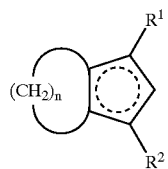

the formula has been shown in, for example, Japanese Patent Laid-open Publication No. 9(1997)-132537 in connection with the use as ligands of metallocene catalysts for olefin polymerization. However, there is no particular teaching having been published as to a crosslink-cyclized cyclopentadiene wherein both $R^1$ and $R^2$ are alkyl groups and as to the process for producing the same. Further, there is no particular synthetic example published for such a compound as far as the inventors' investigations have been made.

OBJECT OF THE INVENTION

The present invention has been made with a view toward solving the above problems of the prior art. It is an object of the present invention to provide a process for producing a crosslink-cyclized cyclopentadiene with high yield under mild conditions without the need to install special apparatus. It is another object of the present invention to provide a crosslink-cyclized cyclopentadiene comprising a cyclopentadiene substituted with two alkyl groups.

It is further objects of the present invention to provide a dihalobis(η-crosslink-cyclized alkyl-substituted cyclopentadienyl)metal compound wherein the above crosslink-cyclized cyclopentadiene is incorporated and to provide a process for producing the same.

SUMMARY OF THE INVENTION

The inventors have made extensive and intensive studies with a view toward solving the above problems. As a result, they have found a novel process for producing a crosslink-cyclized cyclopentadiene with high yield under mild conditions without the need to install special apparatus, wherein a crosslink-cyclized cyclopentenone is reacted with an alkali metal hydride to thereby reduce the same and wherein the thus obtained crosslink-cyclized cyclopentenol is reacted with a dehydrating agent to thereby reduce the same.

In addition, the inventors have specifically found a novel crosslink-cyclized cyclopentadiene comprising a cyclopentadienyl substituted with two alkyl groups.

Moreover, the inventors have found a novel dihalobis(η-crosslink-cyclized alkyl-substituted cyclopentadienyl)metal compound wherein the above crosslink-cyclized cyclopentadiene is incorporated and a process for producing the same. The present invention has been completed on the basis of these findings.

According to the first invention, there is provided a process for producing a crosslink-cyclized cyclopentadiene, comprising the steps of;

reacting a cyclopentenone of the general formula (I) with an alkali metal hydride;

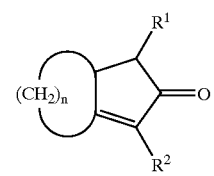

wherein each of $R^1$ and $R^2$ independently represents a hydrogen atom or a linear or branched saturated alkyl group having 1 to 6 carbon atoms, and n is an integer of 3 to 10, to thereby reduce the cyclopentenone (reduction step A) into a cyclopentenol of the general formula (II):

(II)

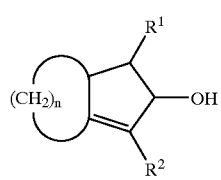

wherein $R^1$, $R^2$ and n are as defined above with respect to the general formula (I); and reacting the cyclopentenol with a dehydrating agent to thereby dehydrate the cyclopentenol (dehydration step B) into a crosslink-cyclized cyclopentadiene of the general formula (III):

(III)

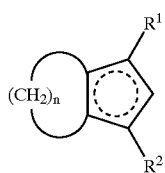

wherein $R^1$, $R^2$ and n are as defined above with respect to the general formula (I), and the broken line in the 5-membered ring denotes that the 5-membered ring has two double bonds.

The alkali metal hydride is preferably an alkali metal borohydride compound, still preferably sodium borohydride or potassium borohydride. The reduction step A is preferably performed at −10 to 100° C. The dehydrating agent is preferably a strong acid. The dehydration step B is preferably performed at −10 to 100° C.

According to the second invention, there is provided a crosslink-cyclized cyclopentadiene of the general formula (IV):

(IV)

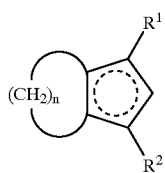

wherein each of $R^1$ and $R^2$ independently represents a linear or branched saturated alkyl group having 1 to 6 carbon atoms, n is an integer of 3 to 10, and the broken line in the 5-membered ring denotes that the 5-membered ring has two double bonds.

According to the third aspect of the present invention, there is provided a dihalobis(η-crosslink-cyclized cyclopentadienyl)metal compound of the general formula (V):

(V)

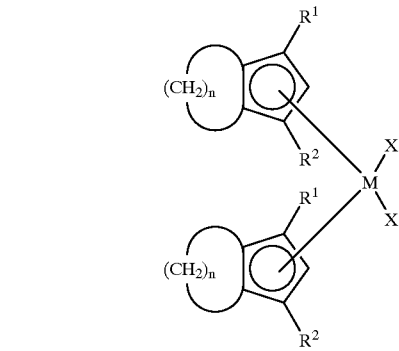

wherein each of $R^1$ and $R^2$ independently represents a linear or branched saturated alkyl group having 1 to 6 carbon atoms; n is an integer of 3 to 10; M represents Ti, Zr or Hf; and X represents a halogen atom selected from among a chlorine atom, a bromine atom, an iodine atom and a fluorine atom.

The dihalobis(η-crosslink-cyclized cyclopentadienyl) metal compound of the general formula (V) according to the present invention is obtained by reacting a cyclopentadiene of the general formula (IV) with a metal halide;

(IV)

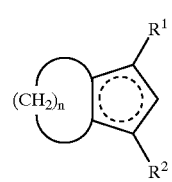

wherein $R^1$, $R^2$ and n are as defined above with respect to the general formula (V), and the broken line in the 5-membered ring denotes that the 5-membered ring has two double bonds, this reaction being performed in the presence of a base.

DETAILED DESCRIPTION OF THE INVENTION

Figure 1:
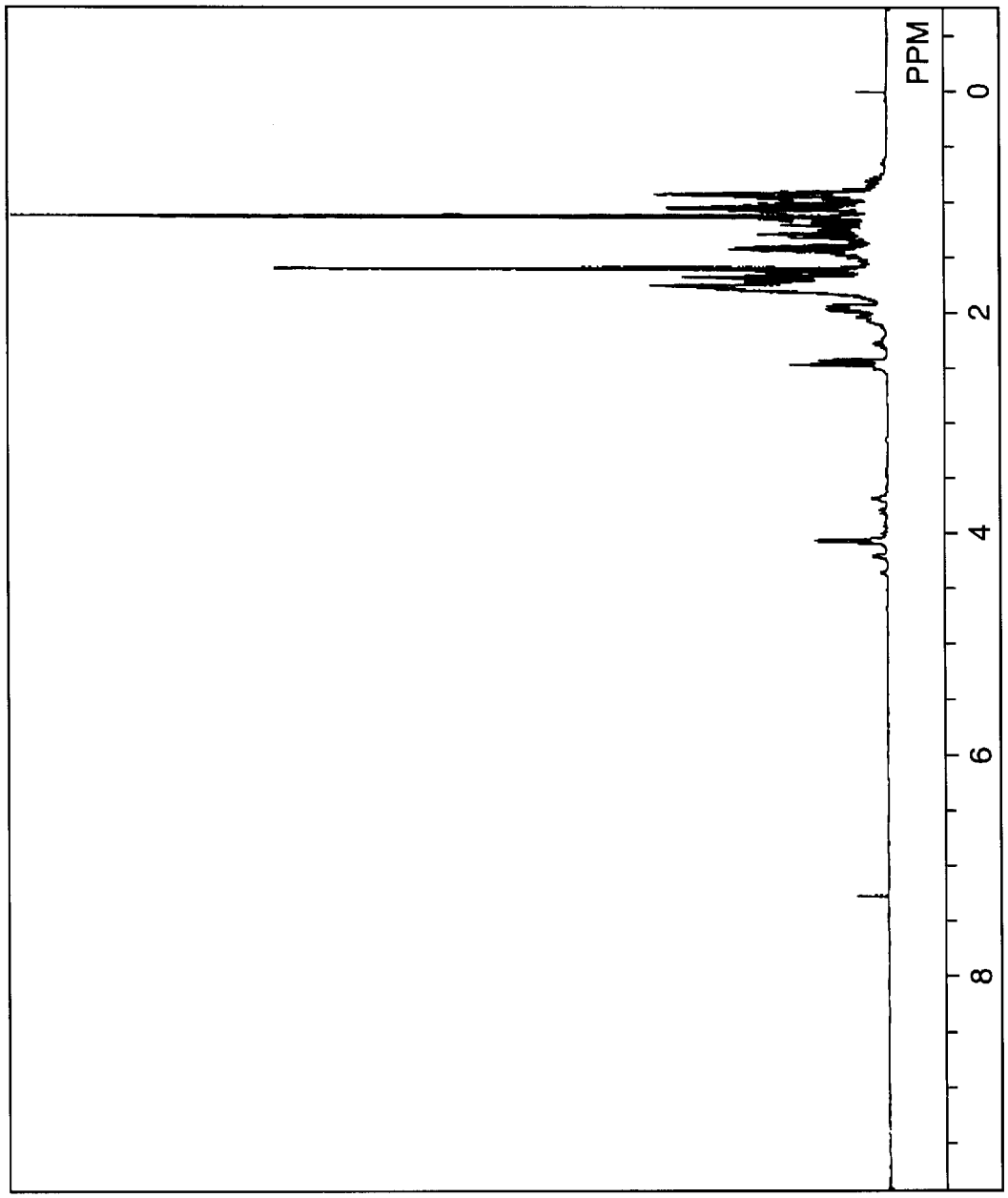
FIG. 1 is an NMR spectrum chart of 7,9-dimethylbicyclo [4,3,0]nona-1(9)-en-8-ol.

The process for producing a crosslink-cyclized cyclopentadiene according to the first invention, the crosslink-cyclized cyclopentadiene according to the second invention and the dihalobis(η-crosslink-cyclized cyclopentadienyl) metal comprising crosslink-cyclized cyclopentadiene according to the third invention together with the process for producing the same will be described in detail below.

[Process for Producing Crosslink-Cyclized Cyclopentadiene]

In the process for producing a crosslink-cyclized cyclopentadiene according to the first invention, first, a cyclopentenone is reacted with an alkali metal hydride to thereby reduce the cyclopentenone (reduction step A) into a cyclopentenol. Thereafter, the cyclopentenol is reacted with a dehydrating agent to thereby dehydrate the cyclopentenol (dehydration step B) into a crosslink-cyclized cyclopentadiene.

Crosslink-Cyclized Cyclopentenone

The crosslink-cyclized cyclopentenone as a starting material of the crosslink-cyclized cyclopentadiene of the present invention is represented by the general formula (I):

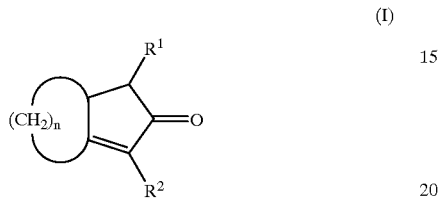

(I)

wherein each of $R^1$ and $R^2$ independently represents a hydrogen atom or a linear or branched saturated alkyl group having 1 to 6 carbon atoms, and n is an integer of 3 to 10.

The linear or branched saturated alkyl group having 1 to 6 carbon atoms, represented by $R^1$ and $R^2$, can be, for example, any of methyl, ethyl, n-propyl, isopropyl, n-butyl, isobutyl, sec-butyl, t-butyl, n-pentyl, isopentyl, sec-pentyl, neopentyl, n-hexyl and isohexyl. The above crosslink-cyclized cyclopentenone represented by the general formula (I) can be, for example, any of; crosslink-cyclized cyclopentenones of the general formula (I) wherein both $R^1$ and $R^2$ are hydrogen atoms, such as bicyclo[3,3,0]octa-1(8)-en-7-one,
bicyclo[4,3,0]nona-1(9)-en-8-one,
bicyclo[5,3,0]deca-1(10)-en-9-one,
bicyclo[6,3,0]undeca-1(11)-en-10-one,
bicyclo[7,3,0]dodeca-1(12)-en-11-one,
bicyclo[8,3,0]trideca-1(13)-en-12-one,
bicyclo[9,3,0]tetradeca-1(14)-en-13-one, and
bicyclo[10,3,0]pentadeca-1(15)-en-14-one;

crosslink-cyclized cyclopentenones of the general formula (I) wherein either of $R^1$ and $R^2$ is an alkyl substituent, such as 6-methylbicyclo[3,3,0]octa-1(8)-en-7-one,
8-methylbicyclo[3,3,0]octa-1(8)-en-7-one,
6-ethylbicyclo[3,3,0]octa-1(8)-en-7-one,
8-ethylbicyclo[3,3,0]octa-1(8)-en-7-one,
6-isopropylbicyclo[3,3,0]octa-(8)-en-7-one,
8-isopropylbicyclo[3,3,0]octa-1(8)-en-7-one,
8-n-butylbicyclo[3,3,0]octa-1(8)-en-7-one,
7-methylbicyclo[4,3,0]nona-1(9)-en-8-one,
9-methylbicyclo[4,3,0]nona-1(9)-en-8-one,
7-ethylbicyclo[4,3,0]nona-1(9)-en-8-one,
9-ethylbicyclo[4,3,0]nona-1(9)-en-8-one,
7-isopropylbicyclo[4,3,0]nona-1(9)-en-8-one,
9-isopropylbicyclo[4,3,0]nona-1 (9)-en-8-one,
9-n-butylbicyclo[4,3,0]nona-1(9)-en-8-one,
8-methylbicyclo[5,3,0]deca-1(10)-en-9-one,
10-methylbicyclo[5,3,0]deca-1(10)-en-9-one,
8-ethylbicyclo[5,3,0]deca-1(10)-en-9-one,
10-ethylbicyclo[5,3,0]deca-1(10)-en-9-one,
8-isopropylbicyclo[5,3,0]deca-1(10)-en-9-one,
10-isopropylbicyclo[5,3,0]deca-1(10)-en-9-one,
10-n-butylbicyclo[5,3,0]deca-1(10)-en-9-one,
9-methylbicyclo[6,3,0]undeca-1(11)-en-10-one,
11-methylbicyclo[6,3,0]undeca-1(11)-en-10-one,
9-ethylbicyclo[6,3,0]undeca-1(11)-en-10-one,
11-ethylbicyclo[6,3,0]undeca-1(11)-en-10-one,
9-isopropylbicyclo[6,3,0]undeca-1(11)-en-10-one,
11-isopropylbicyclo[6,3,0]undeca-1(11)-en-10-one,
11-n-butylbicyclo[6,3,0]undeca-1(11)-en-10-one,
10-methylbicyclo[7,3,0]dodeca-1 (12)-en-11-one,
12-methylbicyclo[7,3,0]dodeca-1 (12)-en-11-one,
10-ethylbicyclo[7,3,0]dodeca-1(12)-en-11-one,
12-ethylbicyclo[7,3,0]dodeca-1(12)-en-11-one,
10-isopropylbicyclo[7,3,0]dodeca-1(12)-en-11-one,
12-isopropylbicyclo[7,3,0]dodeca-1(12)-en-11-one,
12-n-butylbicyclo[7,3,0]dodeca-1(12)-en-11-one,
1-methylbicyclo[8,3,0]trideca-1(13)-en-12-one,
13-methylbicyclo[8,3,0]trideca-1(13)-en-12-one,
11-ethylbicyclo[8,3,0]trideca-1(13)-en-12-one,
13-ethylbicyclo[8,3,0]trideca-1(13)-en-12-one,
11-isopropylbicyclo[8,3,0 ]trideca-1(13)-en-12-one,
13-isopropylbicyclo[8,3,0]trideca-1(13)-en-12-one,
13-n-butylbicyclo[8,3,0]trideca-1(13)-en-12-one,
12-methylbicyclo[9,3,0]tetradeca-1(14)-en-13-one,
14-methylbicyclo[9,3,0]tetradeca-1(14)-en-13-one,
12-ethylbicyclo[9,3,0]tetradeca-1(14)-en-13-one,
14-ethylbicyclo[9,3,0]tetradeca-1(14)-en-13-one,
12-isopropylbicyclo[9,3,0]tetradeca-1(14)-en-13-one,
14-isopropylbicyclo[9,3,0]tetradeca-1(14)-en-13-one,
14-n-butylbicyclo[9,3,0]tetradeca-1(14)-en-13-one,
13-methylbicyclo[10,3,0]pentadeca-1(15)-en-14-one,
15-methylbicyclo[10,3,0]pentadeca-1(15)-en-14-one,
13-ethylbicyclo[10,3,0]pentadeca-1(15)-en-14-one,
15-ethylbicyclo[10,3,0]pentadeca-1(15)-en-14-one,
13-isopropylbicyclo[10,3,]pentadeca-1(15)-en-14-one,
15-isopropylbicyclo[10,3,0]pentadeca-1(15)-en-14-one, and
15-n-butylbicyclo[10,3,0]pentadeca-1(15)-en-14-one; and crosslink-cyclized cyclopentenones of the general formula (I) wherein both $R^1$ and $R^2$ are alkyl substituents, such as 6,8-dimethylbicyclo[3,3,0]octa-1(8)-en-7-one,
6,8-diethylbicyclo[3,3,0]octa-1(8)-en-7-one,
6,8-diisopropylbicyclo[3,3,0]octa-1(8)-en-7-one,
6-methyl-8-n-butylbicyclo[3,3,0]octa-1(8)-en-7-one,
7,9-dimethylbicyclo[4,3,0]nona-1(9)-en-8-one,
7,9-diethylbicyclo[4,3,0]nona-1(9)-en-8-one,
7,9-diisopropylbicyclo[4,3,0]nona-1(9)-en-8-one,
7-methyl-9-n-butylbicyclo[4,3,0]nona-1(9)-en-8-one,
8,10-dimethylbicyclo[5,3,0]deca-1(10)-en-9-one,
8,10-diethylbicyclo[5,3,0]deca-1(10)-en-9-one,
8,10-diisopropylbicyclo[5,3,0]deca-1(10)-en-9-one,
8-methyl-10-n-butylbicyclo[5,3,0]deca-1(10)-en-9-one,
9,11-dimethylbicyclo[6,3,0]undeca-1(11)-en-10-one,
9,11-diethylbicyclo[6,3,0]undeca-1(11)-en-10-one, 9,11-diisopropylbicyclo[6,3,0]undeca-1(11)-en-10-one,
9-methyl-11-n-butylbicyclo[6,3,0]undeca-1(11)-en-10-one,
10,12-dimethylbicyclo[7,3,0]dodeca-1(12)-en-11-one,
10,12-diethylbicyclo[7,3,0]dodeca-1(12)-en-11-one,
10,12-diisopropylbicyclo[7,3,0]dodeca-1(12)-en-11-one,
10-methyl-12-n-butylbicyclo[7,3,0]dodeca-1 (12)-en-11-one,
11,13-dimethylbicyclo[8,3,0]trideca-1 (13)-en-12-one,
11,13-diethylbicyclo[8,3,0]trideca-1(13)-en-12-one,
11,13-diisopropylbicyclo[8,3,0]trideca-1(13)-en-12-one,
11-methyl-13-n-butylbicyclo[8,3,0]trideca-1(13)-en-12-one,
12,14-dimethylbicyclo[9,3,0]tetradeca-1 (14)-en-13-one,
12,14-diethylbicyclo[9,3,0]tetradeca-1(14)-en-13-one,
12,14-diisopropylbicyclo[9,3,0]tetradeca-1(14)-en-13-one,
12-methyl-14-n-butylbicyclo[9,3,0]tetradeca-1(14)-en-13-one,
13,15-dimethylbicyclo[10,3,0]pentadeca-1(15)-en-14-one,
13,15-diethylbicyclo[10,3,0]pentadeca-1(15)-en-14-one,
13,15-diisopropylbicyclo[10,3,0]pentadeca-1(15)-en-14-one, and
13-methyl-15-n-butylbicyclo[10,310]pentadeca-1(15)-en-14-one.

These crosslink-cyclized cyclopentenones can be synthesized by known methods, for example, the method described in J. Am. Chem. Soc., 100, 1799 (1978).

[Reduction Step A]

Alkali Metal Hydride

The alkali metal hydride for use in the reduction step A of the present invention can be, for example, an alkali metal borohydride compound such as sodium borohydride or potassium borohydride, or an alkali metal aluminum alkoxyhydride compound. Of these, sodium borohydride and potassium borohydride are preferred, and sodium borohydride is especially preferred.

It is preferred that the alkali metal hydride be used in a molar amount of 0.5 to 8 times, especially 1 to 4 times, and still especially 2 to 3 times, that of the above crosslink-cyclized cyclopentenone.

Solvent (Reduction Step A)

The reduction reaction of the reduction step A of the present invention is preferably performed in the presence of a solvent. As a suitable solvent, there can be mentioned, for example, an alcohol such as methanol or ethanol, an ether such as tetrahydrofuran, 1,3-dioxolane, dimethoxyethane, dioxane, diethyl ether or dibutyl ether, water and DMF.

The above solvents can be used individually or in combination.

It is generally preferred that the solvent be used in an amount of 1 to 20 parts by weight, especially 3 to 8 parts by weight, and still especially 4 to 6 parts by weight, per 100 parts by weight of alkali metal hydride.

Reaction Condition (Reduction Step A)

In the reaction of crosslink-cyclized cyclopentenone and alkali metal hydride, it is generally preferred that the reaction temperature be in the range of about −10 to 100° C., especially −10 to 80° C., and still especially 0 to 30° C. It is generally preferred that the reaction time be in the range of 30 min to 24 hr, especially 2 to 8 hr. This reaction is preferably performed in an atmosphere of inert gas such as nitrogen gas.

The reduction reaction can be selectively advanced by carrying out the reaction of crosslink-cyclized cyclopentenone and alkali metal hydride under the above conditions to thereby enable obtaining the desired crosslink-cyclized cyclopentenol with high yield.

After the completion of the reaction, the product can be obtained by, for example, sequentially performing acid neutralization of a solution containing the reaction product, isolation and purification. Instead, without isolating the reaction product, the solution containing the reaction product can directly be subjected to the subsequent dehydration reaction (B) of formed crosslink-cyclized cyclopentenol. The product yield is generally in the range of about 70 to 90% based on the cyclopentenol.

The thus obtained product is crosslink-cyclized cyclopentenol of the general formula (II):

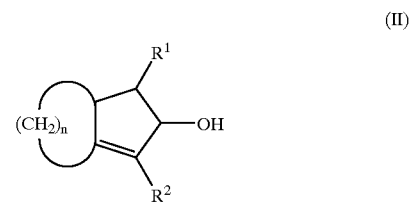

(II)

wherein $R^1$, $R^2$ and n are as defined above with respect to the general formula (I).

[Dehydration Step B]

Dehydrating Agent

The dehydrating agent for use in the dehydration reaction of cyclopentenol of the general formula (II) in the dehydration step B of the present invention is preferably an acid dehydrating agent, still preferably a strong acid. As the acid dehydrating agent, there can be mentioned, for example, hydrochloric acid, paratoluenesulfonic acid and sulfuric acid.

It is preferred that the dehydrating agent be used in a molar amount of 0.01 to 1.0 time, especially 0.05 to 0.5 time, and still especially 0.10 to 0.25 time, that of the above crosslink-cyclized cyclopentenol.

Solvent (Dehydration Step B)

The dehydration reaction of the dehydration step B of the present invention is preferably performed in the presence of a solvent. Any solvents can be employed as long as they are inert to the reaction. For example, solvents used in the above reduction step A and hydrocarbon solvents can be employed as the solvent. In particular, in the dehydration step B, there can preferably be employed polar solvents capable of oil/water separation, for example, ether solvents such as tetrahydrofuran, 1,3-dioxolane, dimethoxyethane, dioxane, diethyl ether and dibutyl ether. These solvents can be used individually or in combination.

It is generally preferred that the solvent be used in an amount of 1 to 20 parts by weight, especially 3 to 10 parts by weight, and still especially 5 to 7 parts by weight, per 100 parts by weight of crosslink-cyclized cyclopentenol.

Reaction Condition (Dehydration Step B)

In the reaction of crosslink-cyclized cyclopentenol and dehydrating agent, it is generally preferred that the reaction temperature be in the range of about −10 to 60° C., especially 0 to 40° C., and still especially 10 to 30° C. It is generally preferred that the reaction time be in the range of 1 to 48 hr, especially 4 to 12 hr. This reaction is preferably performed in an atmosphere of inert gas such as nitrogen gas.

The desired crosslink-cyclized cyclopentadiene can be obtained by carrying out the reaction of crosslink-cyclized cyclopentenol and dehydrating agent under the above conditions.

After the completion of the reaction, the product can be obtained by, for example, sequentially performing neutralization of a solution containing the reaction product, isolation and purification. The product yield is generally in the range of about 70 to 90% based on the cyclopentenone.

The thus obtained product is crosslink-cyclized cyclopentadiene of the general formula (III):

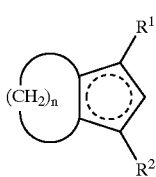

(III)

wherein $R^1$, $R^2$ and n are as defined above with respect to the general formula (I), and the broken line in the 5-membered ring denotes that the 5-membered ring has two double bonds.

The crosslink-cyclized cyclopentadiene obtained by the present invention can be, for example, any of: crosslink-cyclized cyclopentadienes of the general formula (III) wherein both $R^1$ and $R^2$ are hydrogen atoms, such as
  bicyclo[3,3,0]octadiene,
  bicyclo[4,3,0]nonadiene,
  bicyclo[5,3,0]decadiene,
  bicyclo[6,3,0]undecadiene,
  bicyclo[7,3,0]dodecadiene,
  bicyclo[8,3,0]tridecadiene,
  bicyclo[9,3,0]tetradecadiene, and
  bicyclo[10,3,0]pentadecadiene;
crosslink-cyclized cyclopentadienes of the general formula (III) wherein either of $R^1$ and $R^2$ is an alkyl substituent, such as
  6-methylbicyclo[3,3,0]octadiene,
  8-methylbicyclo[3,3,0]octadiene,
  6-ethylbicyclo[3,3,0]octadiene,
  8-ethylbicyclo[3,3,0]octadiene,
  6-isopropylbicyclo[3,3,0]octadiene,
  8-isopropylbicyclo[3,3,0]octadiene,
  8-n-butylbicyclo[3,3,0]octadiene,
  7-methylbicyclo[4,3,0]nonadiene,
  9-methylbicyclo[4,3,0]nonadiene,
  7-ethylbicyclo[4,3,0]nonadiene,
  9-ethylbicyclo[4,3,0]nonadiene,
  7-isopropylbicyclo[4,3,0]nonadiene,
  9-isopropylbicyclo[4,3,0]nonadiene,
  9-n-butylbicyclo[4,3,0]nonadiene,
  8-methylbicyclo[5,3,0]decadiene,
  10-methylbicyclo[5,3,0]decadiene,
  8-ethylbicyclo[5,3,0]decadiene,
  10-ethylbicyclo[5,3,0]decadiene,
  8-isopropylbicyclo[5,3,0]decadiene,
  10-isopropylbicyclo[5,3,0]decadiene,
  10-n-butylbicyclo[5,3,0]decadiene,
  9-methylbicyclo[6,3,0]undecadiene,
  11-methylbicyclo[6,3,0]undecadiene,
  9-ethylbicyclo[6,3,0]undecadiene,
  11-ethylbicyclo[6,3,0]undecadiene,
  9-isopropylbicyclo [6,3,0]undecadiene,
  11-isopropylbicyclo[6,3,0]undecadiene,
  11-n-butylbicyclo[6,3,0]undecadiene,
  10-methylbicyclo[7,3,0]dodecadiene,
  12-methylbicyclo[7,3,0]dodecadiene,
  10-ethylbicyclo[7,3,0]dodecadiene,
  12-ethylbicyclo[7,3,0]dodecadiene,
  10-isopropylbicyclo[7,3,0]dodecadiene,
  12-isopropylbicyclo[7,3,0]dodecadiene,
  12-n-butylbicyclo[7,3,0]dodecadiene,
  11-methylbicyclo[8,3,0]tridecadiene,
  13-methylbicyclo[8,3,0]tridecadiene,
  11-ethylbicyclo[8,3,0]tridecadiene,
  13-ethylbicyclo[8,3,0]tridecadiene,
  11-isopropylbicyclo[8,3,0]tridecadiene,
  13-isopropylbicyclo[8,3,0]tridecadiene,
  13-n-butylbicyclo[8,3,0]tridecadiene,
  12-methylbicyclo[9,3,0]tetradecadiene,
  14-methylbicyclo[9,3,0]tetradecadiene,
  12-ethylbicyclo[9,3,0]tetradecadiene,
  14-ethylbicyclo[9,3,0]tetradecadiene,
  12-isopropylbicyclo[9,3,0]tetradecadiene,
  14-isopropylbicyclo[9,3,0]tetradecadiene,
  14-n-butylbicyclo[9,3,0]tetradecadiene,
  13-methylbicyclo[10,3,0]pentadecadiene,
  15-methylbicyclo[10,3,0]pentadecadiene,
  13-ethylbicyclo[10,3,0]pentadecadiene,
  15-ethylbicyclo[10,3,0]pentadecadiene,
  13-isopropylbicyclo[10,3,0]pentadecadiene,
  15,isopropylbicyclo[10,3,O]pentadecadiene, and
  15-n-butylbicyclo[10,3,0]pentadecadiene; and
crosslink-cyclized cyclopentadienes of the general formula (III) wherein both $R^1$ and $R^2$ are alkyl substituents, such as
  6,8-dimethylbicyclo[3,3,0]octadiene,
  6,8-diethylbicyclo[3,3,0]octadiene,
  6,8-diisopropylbicyclo[3,3,0]octadiene,
  6-methyl-8-n-butylbicyclo[3,3,0]octadiene,
  7,9-dimethylbicyclo[4,3,0]nonadiene,
  7,9-diethylbicyclo[4,3,0]nonadiene,
  7,9-diisopropylbicyclo[4,3,0]nonadiene,
  7-methyl-9-n-butylbicyclo[4,3,0]nonadiene,
  8,10-dimethylbicyclo[5,3,0]decadiene,
  8,10-diethylbicyclo[5,3,0]decadiene,
  8,10-diisopropylbicyclo[5,3,0]decadiene,
  8-methyl-10-n-butylbicyclo[5,3,0]decadiene,
  9,11-dimethylbicyclo[6,3,0]undecadiene,
  9,11-diethylbicyclo[6,3,0]undecadiene,
  9,11-diisopropylbicyclo[6,3,0]undecadiene, 9-methyl-11-n-butylbicyclo[6,3,0]undecadiene,
10,12-dimethylbicyclo[7,3,0]dodecadiene,
10,12-diethylbicyclo[7,3,0]dodecadiene,
10,12-diisopropylbicyclo[7,3,0]dodecadiene,
10-methyl-12-n-butylbicyclo[7,3,0]dodecadiene,
11,13-dimethylbicyclo[8,3,]tridecadiene,
11,13-diethylbicyclo[8,3,0]tridecadiene,
11,13-diisopropylbicyclo[8,3,O]tridecadiene,
11-methyl-13-n-butylbicyclo[8,3,0]tridecadiene,
12,14-dimethylbicyclo[9,3,3,0]tetradecadiene,
12,14-diethylbicyclo[9,3,0]tetradecadiene,
12,14-diisopropylbicyclo[9,3,0]tetradecadiene,
12-methyl-14-n-butylbicyclo[9,3,0]tetradecadiene,
13,15-dimethylbicyclo[10,3,0]pentadecadiene,
13,15-diethylbicyclo[10,3,0]pentadecadiene,
13,15-diisopropylbicyclo[10,3,0]pentadecadiene, and
13-methyl-15-n-butylbicyclo[10,3,0]pentadecadiene.

The double bonds of these diene compounds may contain position isomers as a result of isomerization.

[Crosslink-Cyclized Cyclopentadiene]

Among the crosslink-cyclized cyclopentadienes, the second invention provides crosslink-cyclized cyclopentadienes of the general formula (IV):

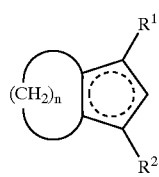

(IV)

wherein each of $R^1$ and $R^2$ independently represents a linear or branched saturated alkyl group having 1 to 6 carbon atoms, n is an integer of 3 to 10, and the broken line in the 5-membered ring denotes that the 5-membered ring has two double bonds. These crosslink-cyclized cyclopentadienes are novel compounds, examples of which include 6,8-dimethylbicyclo[3,3,0]octadiene,
6,8-diethylbicyclo[3,3,0]octadiene,
6,8-diisopropylbicyclo[3,3,0]octadiene,
6-methyl-8-n-butylbicyclo[3,3,0]octadiene,
7,9-dimethylbicyclo[4,3,0]nonadiene,
7,9-diethylbicyclo[4,3,0]nonadiene,
7,9-diisopropylbicyclo[4,3,0]nonadiene,
7-methyl-9-n-butylbicyclo[4,3,0]nonadiene,
8,10-dimethylbicyclo[5,3,0]decadiene,
8,10-diethylbicyclo[5,3,0]decadiene,
8,10-diisopropylbicyclo[5,3,0]decadiene,
8-methyl-10-n-butylbicyclo[5,3,0]decadiene,
9,11-dimethylbicyclo[6,3,0]undecadiene,
9,11-diethylbicyclo[6,3,0]undecadiene,
9,11-diisopropylbicyclo[6,3,0]undecadiene,
9-methyl-11-n-butylbicyclo[6,3,0]undecadiene,
10,12-dimethylbicyclo[7,3,0]dodecadiene,
10,12-diethylbicyclo[7,3,0]dodecadiene,
10,12-diisopropylbicyclo[7,3,0]dodecadiene,
10-methyl-12-n-butylbicyclo[7,3,0]dodecadiene,
11,13-dimethylbicyclo[8,3,0]tridecadiene,
11,13-diethylbicyclo[8,3,0]tridecadiene,
11,13-diisopropylbicyclo[8,3,0]tridecadiene,
11-methyl-13-n-butylbicyclo[8,3,0]tridecadiene,
12,14-dimethylbicyclo[9,3,0]tetradecadiene,
12,14-diethylbicyclo[9,3,0]tetradecadiene,
12,14-diisopropylbicyclo[9,3,0]tetradecadiene,
12-methyl-14-n-butylbicyclo[9,3,0]tetradecadiene,
13,15-dimethylbicyclo[10,3,0]pentadecadiene,
13,15-diethylbicyclo[10,3,0]pentadecadiene,
13,15-diisopropylbicyclo[10,3,0]pentadecadiene, and
13-methyl-15-n-butylbicyclo[10,3,0]pentadecadiene.

The double bonds of these diene compounds may contain position isomers as a result of isomerization.

[Dihalobis(η-Crosslink-Cyclized Cyclopentadienyl) Metal Compound and Process for Producing thereof]

The dihalobis(η-crosslink-cyclized cyclopentadienyl) metal compound according to the third invention and the process for producing the same will now be described.

The dihalobis(η-crosslink-cyclized cyclopentadienyl) metal compound according to the present invention can be synthesized by reacting the above obtained crosslink-cyclized cyclopentadiene of the general formula (IV) with a metal halide in the presence of a base.

Specifically, the dihalobis(η-crosslink-cyclized cyclopentadienyl)metal compound can be synthesized by:

reacting a cyclopentenone of the general formula (I-1) with an alkali metal hydride;

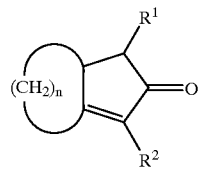

(I-1)

wherein each of $R^1$ and $R^2$ independently represents a hydrogen atom or a linear or branched saturated alkyl group having 1 to 6 carbon atoms, and n is an integer of 3 to 10, to thereby reduce the cyclopentenone (reduction step A) into a cyclopentenol of the general formula (II-1):

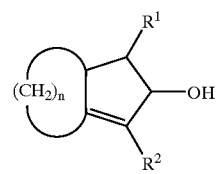

(II-1)

wherein $R^1$, $R^2$ and n are as defined above with respect to the general formula (I-1);

reacting the cyclopentenol with a dehydrating agent to thereby dehydrate the cyclopentenol (dehydration step B) into a crosslink-cyclized cyclopentadiene of the general formula (IV):

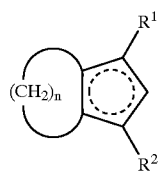 (IV)

wherein R¹, R² and n are as defined above with respect to the general formula (I-1), and the broken line in the 5-membered ring denotes that the 5-membered ring has two double bonds; and reacting the obtained crosslink-cyclized cyclopentadiene with a metal halide in the presence of a base.

In the reaction of the cyclopentadiene with a metal halide in the presence of a base for obtaining the dihalobis(η-crosslink-cyclized cyclopentadienyl)metal compound, use can be made of an inert solvent. For example, the process comprising reacting the crosslink-cyclized cyclopentadiene with a base in a solvent in advance and mixing the resultant reaction mixture with a metal halide suspension is preferably employed.

The base for use in the present invention can be, for example, n-butyllithium or sodium hydride.

As the solvent for use to mix the crosslink-cyclized cyclopentadiene and the base in advance, there can be employed solvents inert to the reaction, for example, an ether such as tetrahydrofuran, 1,3-dioxolane, dimethoxyethane, dioxane, diethyl ether or dibutyl ether, a saturated aliphatic or alicyclic solvent such as n-hexane or cyclohexane and an aromatic solvent such as toluene or benzene.

It is generally preferred that the base be used in a molar amount of 0.8 to 1.5 times, especially 0.9 to 1.2 times, and still especially 0.98 to 1.08 times, that of the above crosslink-cyclized cyclopentadiene.

The temperature at which the crosslink-cyclized cyclopentadiene is reacted with the base is generally in the range of −20 to 50° C., preferably 0 to 30° C. The reaction time is generally in the range of 30 to 48 hr, preferably 5 to 30 hr.

The metal halide compound for use in the present invention can be any of a titanium halide, a zirconium halide and a hafnium halide. Of these, a zirconium halide is preferably employed. For example, the metal halide compound can be any of fluorides, chlorides, bromides and iodides of titaniums (II), (III) and (IV); fluorides, chlorides, bromides and iodides of zirconiums (II), (III) and (IV); and fluorides, chlorides, bromides and iodides of hafniums (II), (III) and (IV). Of these, titanium (IV), zirconium (IV) and hafnium (IV) halides are preferred, and titanium tetrachloride, zirconium tetrachloride and hafnium tetrachloride are especially preferred.

As the solvent for suspending the metal halide compound, there can be employed solvents inert to the reaction, for example, hexane, heptane, toluene and ethers such as tetrahydrofuran, 1,3-dioxolane, dimethoxyethane, dioxane, diethyl ether and dibutyl ether.

It is preferred that the metal halide be used in a molar amount of 0.3 to 0.8 time, especially 0.4 to 0.6 time, and still especially 0.45 to 0.55 time, that of the crosslink-cyclized cyclopentadiene.

The dihalobis(η-crosslink-cyclized cyclopentadienyl)metal compound of the present invention can be obtained by adding the suspension of metal halide to the reaction mixture of crosslink-cyclized cyclopentadiene and base to thereby effect a reaction therebetween. The reaction temperature is generally in the range of −20 to 50° C., preferably 0 to 30° C. The reaction time is generally in the range of 3 to 72 hr, preferably 10 to 48 hr.

The thus obtained dihalobis(η-crosslink-cyclized cyclopentadienyl)metal compound is represented by the following general formula (V), and finds applications as an olefin polymerization catalyst, as a carbometallization agent for acetylene compounds, in the synthesis of a starting material of monohydride homologues and as a vulcanizing agent for silicones and rubbers;

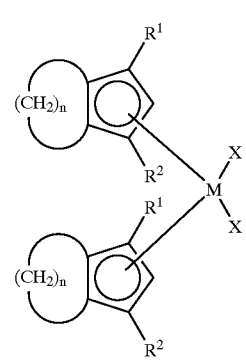 (V)

wherein each of R¹ and R² independently represents a linear or branched saturated alkyl group having 1 to 6 carbon atoms; n is an integer of 3 to 10; M represents Ti, Zr or Hf; and X represents a halogen atom selected from among a chlorine atom, a bromine atom, an iodine atom and a fluorine atom.

The dihalobis(η-crosslink-cyclized cyclopentadienyl) metal compounds of the general formula (V) are novel compounds. As examples thereof, there can be mentioned dihalobis(η-crosslink-cyclized cyclopentadienyl)metal compounds formed by reactions between crosslink-cyclized cyclopentadienes as set forth above as particular compounds of the general formula (IV) and titanium, zirconium and hafnium halides. Preferred products are, for example, dichlorobis(η-crosslink-cyclized cyclopentadienyl)titanium, dichlorobis(η-crosslink-cyclized cyclopentadienyl) zirconium and dichlorobis(η-crosslink-cyclized cyclopentadienyl)hafnium.

EFFECT OF THE INVENTION

The process for producing a crosslink-cyclized cyclopentadiene according to the first invention enables producing a crosslink-cyclized cyclopentadiene with high yield under mild conditions without the need to install special apparatus. Further, the second invention enables providing a novel crosslink-cyclized cyclopentadiene. Still further, the third invention enables providing a dihalobis(η-crosslink-cyclized cyclopentadienyl)metal compound containing the above crosslink-cyclized cyclopentadiene as ligands.

EXAMPLE

Example 1

[Synthesis of 7,9-dimethylbicyclo[4,3,0]nona-1(9)-en-8-ol]

Methanol (4 g) solution containing 1.64 g (10 mmol) of 7,9-dimethylbicyclo[4,3,0]nona-1(9)-en-8-one prepared by the method of J. Am. Chem. Soc., 100, 1799 (1978) was dropped over a period of 10 min into a suspension obtained by suspending 0.76 g (20 mmol) of sodium borohydride in 5 g of tetrahydrofuran (THF). The mixture was agitated at room temperature (25° C.) for 4 hr. The thus obtained reaction mixture was cooled to 10° C. or below, and 10 g of 2 N hydrochloric acid was dropped thereinto so as to effect neutralization with the pH value adjusted to 7. 10 g of ethyl acetate was added to the reaction mixture. An organic layer was separated, washed with water and dried over sodium sulfate. The sodium sulfate was filtered off, and the solvent was distilled off in vacuum. Thus, 1.94 g of colorless oily compound was obtained (73% purity and 85% yield).

The thus obtained compound was incorporated in $CDCl_3$ and analyzed by $^1H$—NMR (400 MHz). It was found that the compound was 7,9-dimethylbicyclo[4,3,0]non-1(9)-en-8-ol. Spectrum chart obtained by the $^1H$—NMR (400 MHz) analysis is shown in FIG. 1.

[Synthesis of 7,9-dimethylbicyclo[4,3,0]nonadiene]

2 g of 2 N hydrochloric acid was dropped into a solution obtained by dissolving 3.38 g (15 mmol) of the above obtained 7,9-dimethylbicyclo[4,3,0]non-1(9)-en-8-ol in 10 g of cyclohexane and 10 g of THF, and agitated at room temperature (25° C.) for 9 hr. A saturated aqueous solution of $NaHCO_3$ (4 mmol) was added to the reaction mixture so as to adjust the pH value to 9. 10 g of cyclohexane was added to the resultant reaction mixture. An organic layer was separated, washed with water and dried over sodium sulfate. The sodium sulfate was filtered off, and the solvent was distilled off in vacuum. Thus, 3.15 g of colorless oily compound was obtained. The purity was 63%, and the yield was 90% based on the 7,9-dimethylbicyclo[4,3,0]nona-1(9)-en-8-ol.

Figure 2:
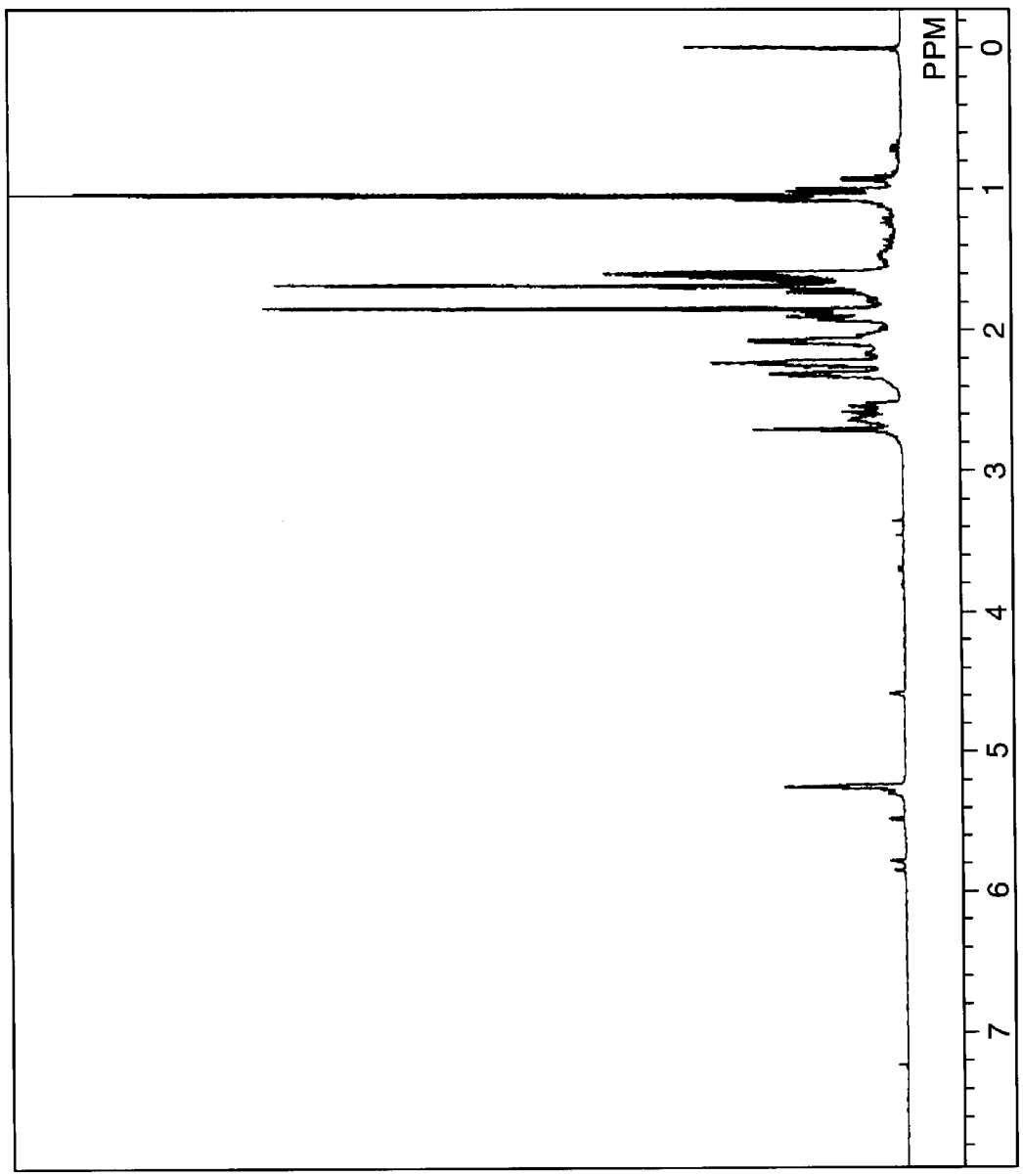
FIG. 2 is an NMR spectrum chart of 7,9-dimethylbicyclo [4,3,0]nonadiene.

The thus obtained compound was incorporated in $CDCl_3$ and analyzed by $^1H$—NMR (400 MHz). It was found that the compound was 7,9-dimethylbicyclo[4,3,0]nonadiene. Spectrum chart obtained by the $^1H$—NMR (400 MHz) analysis is shown in FIG. 2.

Example 2

[Synthesis of dichlorobis{7,9-dimethylbicyclo[4,3,0] nonadienyl}zirconium]

A THF (6 g) solution containing 2.35 g (10 mmol) of 7,9-dimethylbicyclo[4,3,0]nonadiene synthesized in the same manner as in Example 1 was cooled to 5° C. in a nitrogen atmosphere. 6.5 ml (1.6 mmol) of a hexane solution of n-BuLi (10.4 mmol) was dropped into the solution. After the dropping, the reaction mixture was slowly heated up to room temperature (25° C.). At this temperature, the mixture was agitated for 24 hr. Thus, a yellowish-brown suspension was obtained. The obtained yellowish-brown suspension was dropped into a suspension of 1.16 g (5 mmol) of zirconium tetrachloride in 10 g of heptane while maintaining the temperature at 10° C. or below by cooling with ice. Thereafter, the reaction mixture was heated up to room temperature (25° C.) and agitated for 48 hr. Thus, a blackish-brown suspension was obtained. This blackish-brown suspension was filtered to thereby obtain a yellowish-brown solution, from which the solvent was distilled off. Thus, 1.02 g of yellowish-brown viscous oil was obtained. 10 g of heptane was added to the yellowish-brown viscous oil. Precipitated crystal was collected by filtration. Thus, 20 mg of desired crystal was obtained. The purity was about 90%, and the yield was 1% based on the 7,9-dimethylbicyclo[4,3,0]nonadiene.

Figure 3:
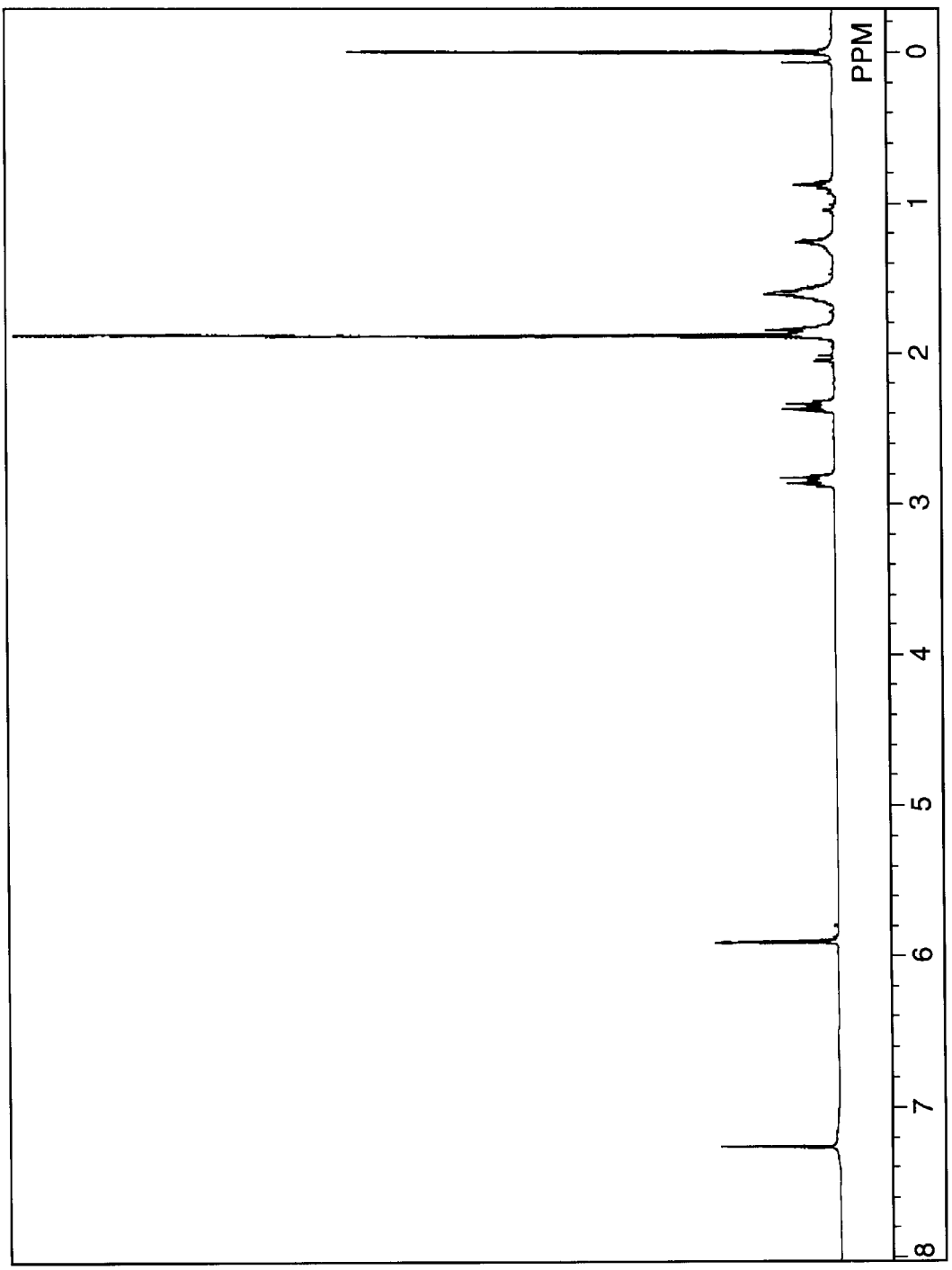
FIG. 3 is an NMR spectrum chart of dichlorobis{7,9-dimethylbicyclo[4,3,0]nonadienyl} zirconium.

The thus obtained compound was incorporated in $CDCl_3$ and analyzed by $^1H$—NMR (400 MHz). It was found that the compound was dichlorobis{7,9-dimethylbicyclo[4,3,0] nonadienyl}zirconium. Spectrum chart obtained by the $^1H$—NMR (400 MHz) analysis is shown in FIG. 3.

What is claimed is:

1. A process for producing a crosslink-cyclized cyclopentadiene, comprising the steps of:

reacting a cyclopentenone of the general formula (I) with an alkali metal hydride;

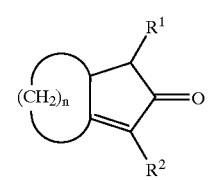

(I)

wherein each of $R^1$ and $R^2$ independently represents a hydrogen atom or a linear or branched saturated alkyl group having 1 to 6 carbon atoms, and n is an integer of 3 to 10, to thereby reduce the cyclopentenone (reduction step A) into a cyclopentenol of the general formula (II):

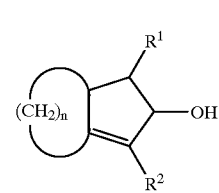

(II)

wherein $R^1$, $R^2$ and n are as defined above; and reacting the cyclopentenol with a dehydrating agent to thereby dehydrate the cyclopentenol (dehydration step B) into a crosslink-cyclized cyclopentadiene of the general formula (III):

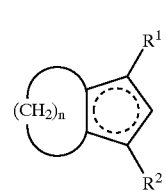

(III)

wherein $R^1$, $R^2$ and n are as defined above, and the broken line in the 5-membered ring denotes that the 5-membered ring has two double bonds.

2. The process as claimed in claim 1, wherein the alkali metal hydride is an alkali metal borohydride compound.

3. The process as claimed in claim 1, wherein the alkali metal hydride is sodium borohydride or potassium borohydride.

4. The process as claimed in any of claims 1 to 3, wherein the reduction step A is performed at −10 to 100° C.

5. The process as claimed in any of claims 1 to 4, wherein the dehydrating agent is a strong acid.

6. The process as claimed in any of claims 1 to 5, wherein the dehydration step B is performed at −10 to 100° C.

7. A dihalobis(η-crosslink-cyclized cyclopentadienyl) metal compound of the formula (V):

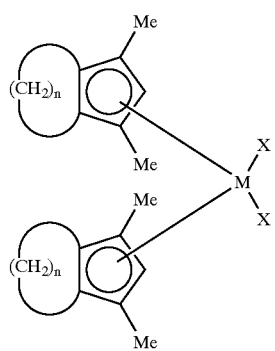

(V)

wherein n is an integer of 3 to 10; M represents Ti, Zr or Hf; and X represents a halogen atom selected from the group consisting of a chlorine atom, a bromine atom, an iodine atom and a fluorine atom.

8. A process for producing a dihalobis(η-crosslink-cyclized cyclopentadienyl)metal compound claimed in claim 7, comprising reacting a cyclopentadiene of the general formula (IV) with a metal halide;

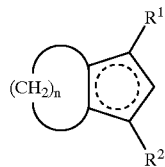

(IV)

wherein each of $R^1$ and $R^2$ independently represents a linear or branched saturated alkyl group having 1 to 6 carbon atoms, n is an integer of 3 to 10, and the broken line in the 5-membered ring denotes that the 5-membered ring has two double bonds, said reaction being performed in the presence of a base.

* * * * *